US005668998A

United States Patent [19]
Mason et al.

[11] Patent Number: 5,668,998
[45] Date of Patent: Sep. 16, 1997

[54] APPLICATION FRAMEWORK OF OBJECTS FOR THE PROVISION OF DICOM SERVICES

[75] Inventors: Donald Mason, Garland; Betsy Ann Zimmerman, Plano, both of Tex.

[73] Assignee: Eastman Kodak Company, Rochester, N.Y.

[21] Appl. No.: 429,397

[22] Filed: Apr. 26, 1995

[51] Int. Cl.$^6$ ........................................... G06F 7/06
[52] U.S. Cl. ................ 395/701; 395/702; 395/680; 395/683; 395/924
[58] Field of Search ........................ 395/680, 683, 395/702, 701, 924

[56] References Cited

U.S. PATENT DOCUMENTS

| | | | |
|---|---|---|---|
| 5,117,351 | 5/1992 | Miller | 395/650 |
| 5,119,444 | 6/1992 | Nishihara | 382/45 |
| 5,289,577 | 2/1994 | Gonzales et al. | 395/163 |
| 5,339,433 | 8/1994 | Frid-Nielsen | 395/700 |
| 5,408,659 | 4/1995 | Cavendish et al. | 395/650 |
| 5,481,601 | 1/1996 | Nazif et al. | 379/207 |
| 5,513,101 | 4/1996 | Pinsky et al. | 364/401 |
| 5,537,630 | 7/1996 | Berry et al. | 395/155 |
| 5,544,302 | 8/1996 | Nguyen | 395/161 |

OTHER PUBLICATIONS

Digital Imaging and Communications in Medicine (DICOM); Part 1 and overview, NEMA Standards Publications PS3.1(199x), pp. 1-7, 9, 11, 13 and 15, Mar. 27, 1992.

Primary Examiner—Alvin E. Oberley
Assistant Examiner—Michael T. Richey
Attorney, Agent, or Firm—William F. Noval

[57] ABSTRACT

A application program interface is provided to a toolkit framework of service objects which enable rapid creation of application computer programs which implement the services and protocol of the Digital Imaging and Communication in Medicine (DICOM) standard. A framework of service objects is provided which enables a programmer to easily develop application methods which provide DICOM services or other custom services. An object-oriented application interface is provided. The service objects provide a familiar connection between the familiar DICOM standard service objects and a group of associated methods within the framework. The associated methods work together to provide a DICOM service. Service Class User and Service Class Provider objects manage service object communications and are derived from baseclasses in the framework.

7 Claims, 3 Drawing Sheets

APPLICATION FRAMEWORK OF OBJECTS FOR THE PROVISION OF DICOM SERVICES

BACKGROUND OF THE INVENTION

1. Field of the Invention

The present invention relates to the field of digital medical imagery and more particularly to a application interface to the provision of Digital Imaging Communications in Medicine (DICOM) services. A framework of service objects is provided which enables a programmer to easily develop application methods which provide DICOM services or other custom services. An object-oriented application interface is provided. The objects provide a map between DICOM standard service objects and a group of associated objects within a framework. The associated service objects work together to provide a DICOM service. The service objects comprise a method or a computer program which operates in conformance with the DICOM standard.

2. Description of the Related Art

Modern hospitals and diagnostic clinics use medical imagery workstations to access digitized medical imagery derived from a variety of imagery source devices or imagery "modalities." Multiple imagery source devices may be connected via hospital information networks to hospital devices such as viewing workstations, film printers, or optical storage devices. Hospitals typically use a Picture Archival and Communication Systems (PACS) to import and manipulate imagery. PACS are only partial solutions to providing cost effective health care. In order to facilitate the medical professional's use of the complex PACS, and to reduce costs of using such a system, industry personnel have developed the Digital Imagining Communications in Medicine or "DICOM" standard.

The DICOM standard describes a protocol for medical imaging communication. DICOM is based upon the Open System Interconnect (OSI) reference model, which defines a 7-layer protocol model and is well-known to those of skill in the art. DICOM is an "application-level" standard. That is, the DICOM standard is implemented inside the seventh (7th) or uppermost level of the OSI model, the application level. DICOM provides standardized formats for images, a common information model, application service definitions, and a protocol for communication. The DICOM standard is an industry-wide standard, well known to those of skill in the art.

The DICOM standard specifies certain services and a protocol for the provision of those services to PACS users. DICOM, however, does not provide applications to provided DICOM service, or which conform to the DICOM standard protocol. Application development is left to the imagination and determination of system designers and application programmers, who must create, develop, implement (write code), and debug thousands of lines of computer code to develop applications which provide DICOM services and conform to the DICOM standard protocol.

Thus there is a need for a application programmers' interface to assist in development of computer applications which provide DICOM services and conform to the DICOM standard protocol. Such a toolkit would save hundreds of programming hours formerly necessary to write application programs in conformance with the DICOM standard.

SUMMARY OF THE INVENTION

The present invention presents an Application Programmers Interface (API) which maps the DICOM standard services menu onto a framework of service interface objects which perform a selected DICOM services within or between PACS networks. The present invention provides a framework of service interface objects which map onto a service described in the DICOM standard. Each service interface object, when instantiated, is uniquely associated with a user handler and a provider handler. The association with a user/provider handler pair enable the pair to "handle" communications for the associated service interface object.

The toolkit provides access to the services described in the DICOM standard. Access to DICOM services is provided by an object-oriented mapping of DICOM services to service interface objects. The user/provider handler maps the service interface object to software applications which implement selected services within a PACS. The natural mapping presents DICOM services to service interface objects, and presents the toolkit framework to the user in the context of the familiar and well known DICOM standard. This natural mapping between the DICOM standard and the toolkit framework of service interface objects facilitates comprehension and use of the framework.

A service interface object encapsulates the functions necessary to perform the particular DICOM service which it represents. For example, the DICOM STORE service is represented by a service interface object called IMAGE. The IMAGE service interface object encapsulates the functions necessary to perform a DICOM STORE service. The IMAGE service interface object is instantiated with or without modification. An instantiation of a service object creates a unique relationship between the instantiated Service object and a Service Class Provider (SCP) and Service Class User (SCU) pair. The SCP/SCU pair provide scheduling of events and messages to perform the requested service.

SCU issues a message requesting the desired service and SCP returns a message in response to the request. The SCU/SCP pair facilitate communications associated with the objectified service. The SCU/SCP pair exist as long as the associated service interface object remains instantiated. The SCU/SCP pair ensure that messages and events are in appropriate DICOM standard format in conformance with the DICOM standard protocol.

Handler objects (SCUs/SCPs) enable an application to send and return calls to and from other applications, thus, providing an object-oriented register callback function. A SCU/SCP (service user handler/service provider handler) pair exists for each DICOM user service. The SCU, service user handler initiates a DICOM message service request. The SCP, service provider handler responds to the service request. A Service Interface Object (SIO) is derived to encapsulate information and data such as an image object. SIOs provide access to an image being stored in response to a DICOM STORE command. A Validation function is provided which checks the objects and messages generated for conformance with DICOM protocol.

Each service is functionally distributed among atomic service units, each unit representing the smallest portion of a service provided by the present invention. Each atomic unit is represented by a base class, from which service objects are derived. The service object conceptually maps the API representation, presented to the user, to the application world of implementation methods on the computer.

Handler objects provide a set of well known methods. Handler objects contain methods which provide default behavior for providing services, for example, an application is notified when an event occurs. A base class for handler object is provided from which an application subclasses to generate handler objects. Sub-classing enables an application to customize the actions taken by a service interface object.

Provider Handlers exist within a "Verify" provider application. The API provides a base class handler object which provides a default functionality. The base class enables an application developer to create sub-classes with a unique version of any of the base class objects. The Provider Handler is an application object. The methods contained in the Provider Handler object provide a default behavior that comprises a useable interface to a DICOM service. The application can modify the object by creating a sub-class of the class, and writing custom methods for the subclass object to accommodate change.

An advantage of the API toolkit framework of the present invention is that the framework of the present invention provides a set of appropriate DICOM values from which an application programmer selects to create an application which provides a particular DICOM service. The API toolkit framework provides default values which enable an application programmer to easily create computer applications with appropriate parameters which conform to the DICOM standard protocol.

Another advantage of the API tool kit framework is that it enables an application programmer to customize individual objects in the framework or to alter parameter values and object behavior. Modification accommodates changes to the service interface objects provided by the framework. Another advantage of the present invention is that use of service interface objects provided by the toolkit framework substantially reduces the effort hours expended on the development of application programs which conform to the DICOM standard to provide DICOM services on a PACS.

The foregoing aspects, features and advantages, along with other aspects, features and advantages of the present invention will become apparent from the following example of a preferred embodiment of the present invention.

DETAILED DESCRIPTION OF A PREFERRED EMBODIMENT

Figure 1:
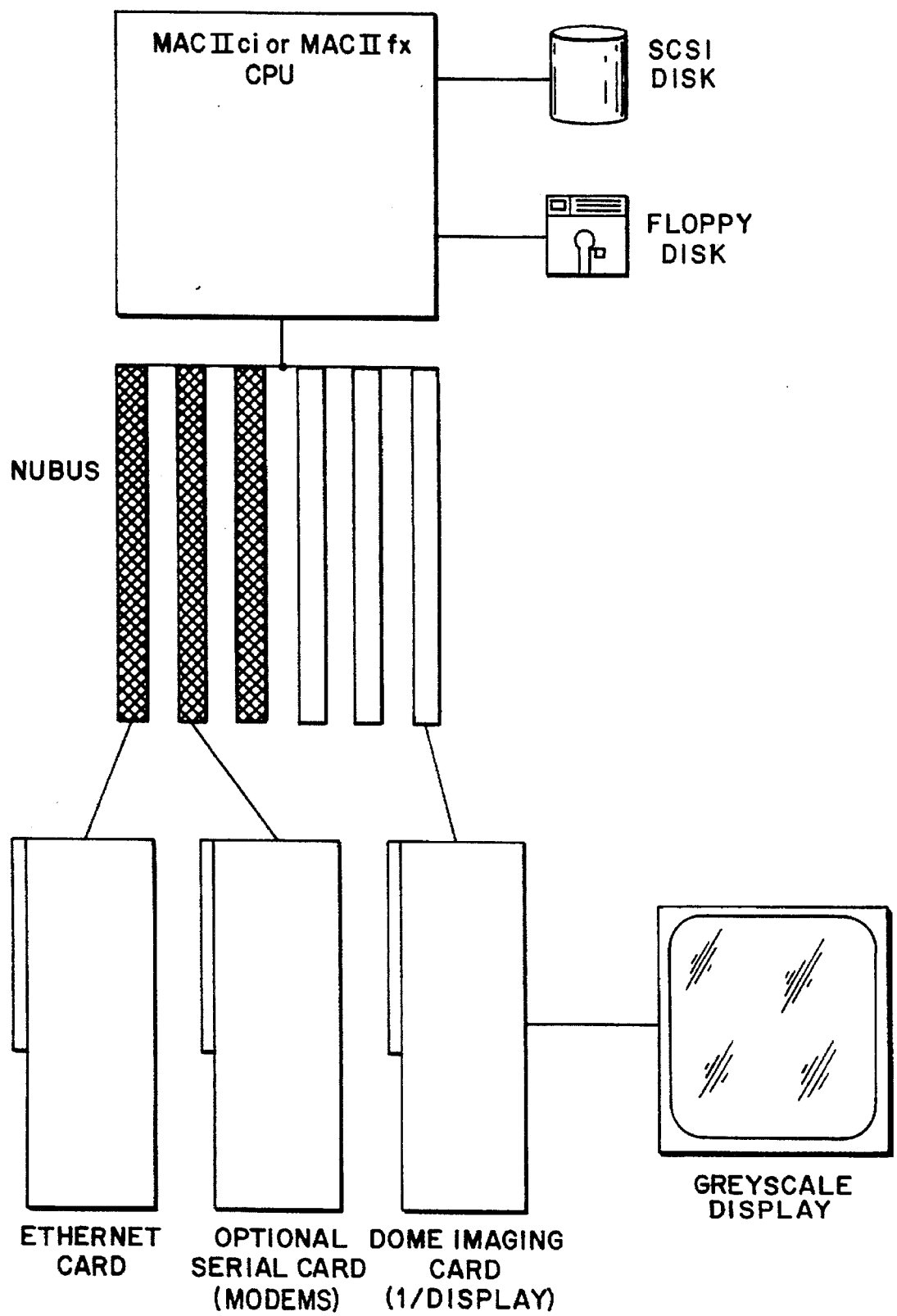
FIG. 1 is a pictorial representation of a hardware environment in an example of a preferred embodiment of the present invention.

The present invention will be further clarified by consideration of the following example, which is intended to be exemplary of the invention and not to be interpreted as a limitation upon the scope or spirit of the present invention.

In a preferred embodiment, the present invention provides an API toolkit to enable applications to rapidly create and develop computer methods which efficiently operate in conformance with DICOM standard protocol. The toolkit provides a framework of objects which map onto the services described in the DICOM standard. The toolkit framework objects selected by the application are modified to create a new method having characteristics the same as or different from the characteristics of the program stored in the selected objects.

The API Toolkit comprises five layers of software. The five layers are machine/transport independent transport layer, association layer, presentation layer, service primitives layer and an information object layer. The toolkit provides the following services: General association initialization and shutdown; Buffer movement into/out out of an association; Element construction via buffer parsing or application creation. (The types of elements having this behavior are specified in DICOM Part 5); Message 'editing' via element addition or removal; Command or response construction; Command or response delivery; Information Object (IO) construction, validation, sending (composite IO); remote attribute setting/getting (normalized IO); remote actioning (normalized IO); IO Definition/Construction and use during validation; lower-level syntax validation using a data dictionary; IO semantics; and Information Model construction and use during the validation of query construction/parsing.

The following is a description of basic features in each of the five layers of the API DICOM toolkit:

(1) The machine/transport independent transport layer unifies the radically different presentations of the MACTCP, BSD sockets and TLI into one event-driven application programmer's interface encapsulated by the class 'Connection'. The 'Connection' provides capabilities to open or close connections via a generic 'PresentationAddress' object. Data flows into and out of connections via an event driven object known as an 'IoLink'. The IoLink provides services similar to those found in typical c++ IoStreams implementations, based on the Kodak Health Imaging Systems-MPAX VBUF structure. This structure provides a complete means to reference and use dynamically allocated memory, 'constant' (static or stack-based memory) or embedded storage within a buffer itself.

(2) The association layer provides association functionality for opening, transferring data over and closing an association. The association layer facilitates reading of previously configured Unique Identifier (UID) information, which enables a PACS to generically interpret third-party vendor UIDs. The presentation layer provides a means for 'canonical' negotiation of: presentation context, implementation of a UID/Class/description, asynchronous transfer window sizes, and SCP-SCU roles. The association layer provides event-driven delivery of asynchronous information.

(3) The presentation layer implements the syntactic functionality in DICOM part 5, DICOM part 6 and static IO/Module semantic specifications in DICOM Part 3. This comprises the capability to encode and decode DICOM message elements and to validate message elements against a data dictionary, module definition and Information Object definition. Encode/Decode (ED) provides support for generic elements (including a Sequence of Items). ED also includes support for specific element encoding/decoding for the following types: Application Entity; Age String; Attribute Tag; Code String; Date; Decimal String; Floating Point Single; Floating Point Double; Integer String; Long String; Long Text; Other Byte; Other Word; Person Name; Short String; Signed Long; Signed Short; Short Text; Time; UID; Unsigned Long; and Unsigned Short. ED includes classes with the following method types: Create; Destroy; Encode; Decode; Insert (sub-object); Remove (sub-object); Find (sub-object); Compare against (explicit or wild card) value; and Embedded support for multiple values and enumerated values where needed.

A Data Dictionary is provided which enables verification of element types (e.g., missing elements, improper zero-length elements, etc.). Verification includes determination of conditional types and corresponding verification of resulting element types. Within each implicit, enumerated value inclusion, multi-value count restrictions and value format (e.g. formats for date, time, person age, etc.) are verified. For defaultable types, data dictionary values are presented for missing elements. The determination of module usage type and subsequent back-verification of element types is provided. The data dictionary layer is oriented toward event-driven delivery of asynchronous information.

(4) The service primitives layer implements the functionality described in DICOM Part 7 (Message Exchange Services). The service primitives layer provides the ability to create a command or corresponding status for each service primitives command type. The service primitives layer provides a means to define and use DICOM transactions and relate them to ACSEs. A throttle window is also provided. This layer also provides generic features within composite service primitives commands and status. The service primitives layer provides normalized service primitives, commands and status. The generic features involved when creating objects, Setting attributes, Getting attributes and deleting objects). Each command and status has certain special element requirements such as status return codes. This layer is also oriented toward event-driven delivery of asynchronous information.

(5) The Information Object layer implements the functionality described in DICOM Part 4 (Services). This encompasses composite as well as normative information objects. The minimal list of objects included are:
Composite
  STORE
    image type:
Normative
  PRINTING:
    Film Session, Film Box, Image Box, Printer, Print Job,
    Basic Annotation, Advanced Annotation, Graphics Primitive DICOM Test Tools are provided which enable testing product robustness in dealing with DICOM information. DICOM test tools facilitate the generation of DICOM test images, storing DICOM test images in files and sending/receiving DICOM test images over an association.

The association layer provides a means to assign attributes to static UIDs (e.g. transfer syntax, abstract syntax, etc.). One of the attributes is 'vendor type'. Thus, the association layer enables mapping third-party vendor UIDs to/from local PACS UIDs. For example, in a particular PACS, local UIDs are provided by Kodak Health Imaging Systems. UIDs which are imported from another (third-party) vendor, are interpreted by the association layer. The association layer enables configuration of a third-party HID into Kodak Health Imaging Systems product applications local UID terms. The association layer provides the ability to negotiate SCP-SCU Roles and an Asynchronous Throughput (Throttle) Window.

The association layer implements the negotiation policy outlined by the DICOM standard. A user may configure multiple transfers in a multiple presentation context for a single abstract syntax, enabling an application to transfer images in different formats over the same association (e.g. compress high-resolution images and leave uncompressed low-resolution images).

The presentation layer provides a means to support default values. Default values provide an additional means by which an application can function without interpreting information embodied within a DICOM message. The presentation layer limits the means by which conditional types are checked in a message. Checking rules use conditional types of the following form:

Element X Exists; Element X value has value Y; Element X value matches pattern Y; Element X value=Element Y value; SOP Class Attribute=value 'AND', 'OR', 'NOT' combinations of any of the above The DICOM standard places no limitation upon rules used to express conditions. The presentation layer does not fully determine if the condition for the module requirement type has been met. For example, the 'contrast-bolas' module is included only if the patient for the image has been injected with a contrast agent. The presentation layer detects when certain elements appear in a message and maps the elements to a particular module (one element appears in at most one module within a given information object), which implies that the module's condition has, at least trivially, been met. Verifying that element requirements type 1 and 2 conditions are met for other elements in the module is then enabled. At most, previous types of limited condition determination will be a module requirement type determination provided in the toolkit.

DICOM protocol enables a given element to exist in more than one module within the same Information Object. Semantics for that element should be precisely the same in each of the modules. Without loss of generality and to simplify design, the toolkit provides a rendition of a module such that (for example) row, column (example elements that have this characteristic) appear in their own module. The presentation layer enables a user of a particular DICOM message to encode the message at any given time. The presentation layer enables multiple users read-only-access to an object while the object is being streamed. The presentation layer will verify minimum/maximum number of items in a sequence as a semantics issue.

The toolkit enables interpreting of normalized information object definition module definitions for event SOPs, such that an event (SOP module) contains any attribute from the corresponding IO and the requirement type is '—/3' (per DICOM, 'adding elements does not reduce conformance'). This enables event SOP definitions to be represented in the same manner as a composite IO module definition.

An application can ignore extra elements, or, the application can use the extra elements. However, it can occur that a 'discharge' time is specified without a specified 'discharge' date in a 'Patient created' event. An application interprets one input event, because of inclusion of extra elements, as multiple 'application' input events (in this case a 'Patient created' and a 'Patient discharged' event). The toolkit provides a means for the application to infer which input events have been communicated via the extra elements (via a mapping of element to SOP module definition). The toolkit also provides a means to verify the requirement types of the extra elements under their (natural) event 'slot'. This eliminates the need for an application to establish a second requirement type (i.e. the requirement type for 'optional' elements within a particular module). In a preferred embodiment all other normalized IO attributes are treated as type 3 for each event.

Preferred Hardware Environment

Turning now to FIG. 1, a block diagram of the hardware environment, for one example of a preferred embodiment of the present invention comprises any of the following hardware platforms and associated operating systems, which are all well known to persons of ordinary skill in the art of computer hardware: Apple Macintosh System 7, Sun Spar 4.1.x+Solaris 2.3+ and Motorola System V(147 and 167 boards).

The present invention preferably resides on a Macintosh computer which provides a digital processor and memory for calculations and storage. In an illustrative example of a preferred embodiment, a graphic user interface uses the windowing capabilities of the Apple Macintosh System 7 Operating System. A preferred embodiment provides a pointer device, a keyboard, soft keys, dialog boxes, icons, action or information messages, postage stamps, and advanced navigation techniques. An illustrative example of a preferred embodiment differs from the conventional environment in that the present invention provides a user-friendly approach to interacting with the system through "direct" manipulation of the toolkit framework objects.

Preferred Software Environment

A preferred embodiment exist along with the Macintosh operating system 7 software environment. The Macintosh operating system and associated hardware provide a host environment for software computer program applications as shown running on the computer in FIG. 1. A preferred embodiment comprises a local database which provides user access and organization of image and report files. The software microfiche appendix presents object scenarios which illustrate how an application implements a DICOM service; code examples illustrating how an application implements a DICOM service, and a listing of objects and object relationships which exist in a preferred embodiment of the toolkit.

Operational Overview

DICOM service users send and receive medical information such as images, print pages, patient demographics, hospital or radiology clinic visits, scheduled studies and diagnostic results. Images are copied remotely using the DICOM STORE service. Queries for images can be performed using the DICOM QUERY/RETRIEVE service. Print pages are created, manipulated or printed on a remote printer using the DICOM PRINT MANAGEMENT service. Patient, visit, study and results information are remotely received from a remote data base residing in another computer.

DICOM standard functions are available in a framework of objects, thus common DICOM functions need be implemented only once and placed in the framework for future use. An implemented DICOM service, or set of objects which implement the DICOM service, is placed in the framework of objects. The DICOM service collection of objects is then available to an application programmer accessing the framework in implementing the same or a similar DICOM service.

In the present invention, DICOM standard services are implemented by objects or o methods which exist within a toolkit framework. In a preferred embodiment, the framework is divided into application subsystems and internal subsystems. Application subsystems are used directly by application entities, for example, vendor product applications. Application entities directly access internal services to provide messages which conform to DICOM standard protocol. Application subsystems provide a framework of objects mapped to an abstract form of DICOM services. The application framework and associated mapping to DICOM services provides an application interface to the toolkit framework. The application interface simplifies creation of an application program which provides DICOM services and conforms to DICOM protocol.

Figure 2:
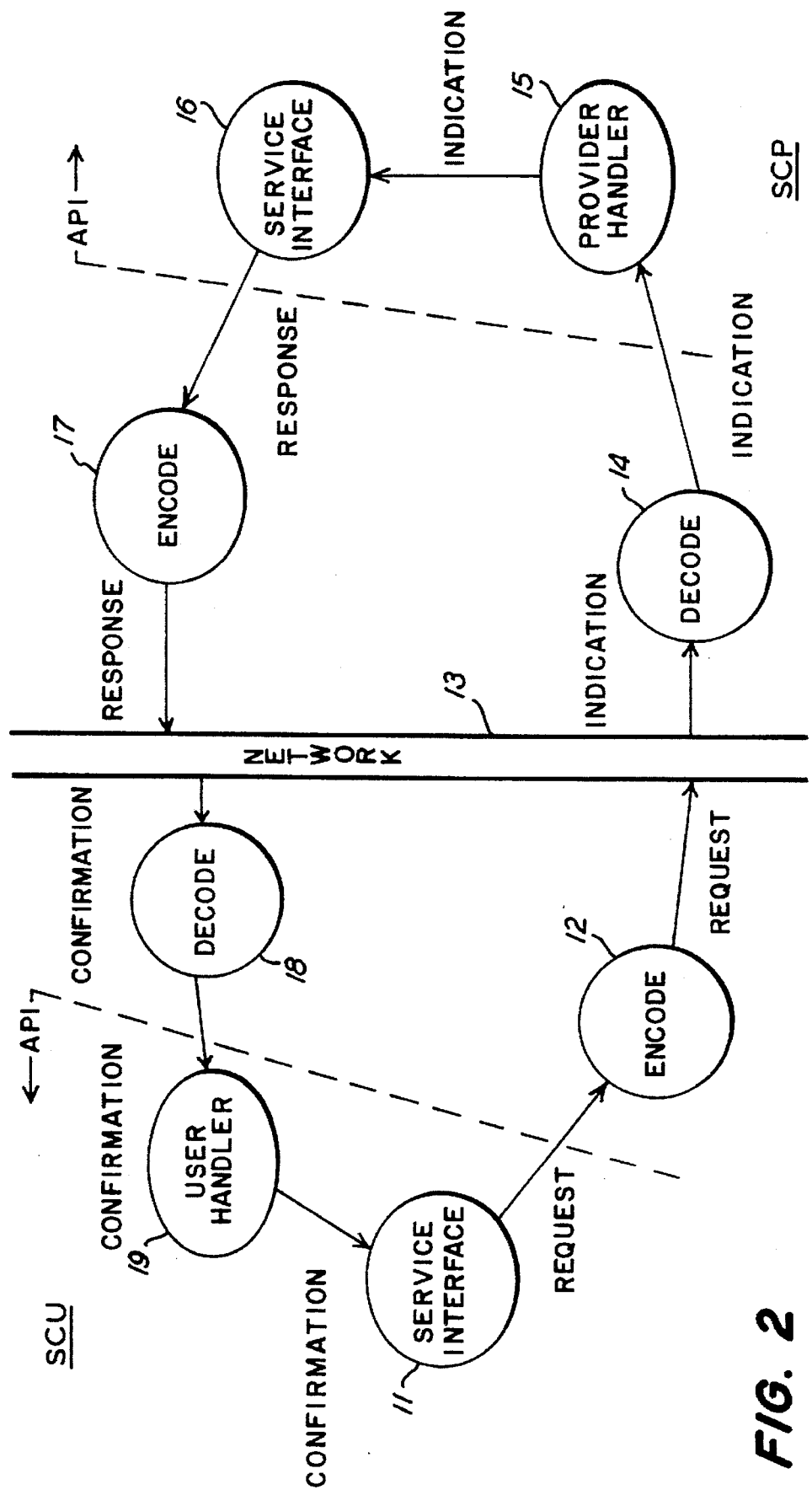
FIG. 2 is an operational overview of how the preferred method implements a service.

Turning now to FIG. 2, in a example of an operational scenario, a DTServiceInterface object 11 initiates a request. This is true for all service classes. The only difference between a verify request and one of the print requests is the particular subclass of the DTServiceInterface object that is chosen by the application developer. The outgoing message is called a "Request". The request is encoded 12 into a DICOM message. This involves two processes. First, the message is formulated into the DICOM Toolkit's own internal representation which we call an element list. Each individual attribute that together will compromise the message is represented in this list.

The elements in the list then each in ram, dumped into packets specified by the DICOM protocol. The elements themselves, each know how to format themselves correctly. These packets are transmitted across a network 13 (ethernet, fddi, etc.) to a DICOM service provider.

The incoming packets are decoded 14 by the service provider 15, and an element list that is identical to the one that was transmitted is created by the provider. The incoming message is called an "Indication." The decoding process determines the message type. This information is used to route the message to the correct DTProviderHandler. Store Indication messages are routed to the DTStoreProviderHandler. Verify Indication messages are routed to the DTVerificationProviderHandler, etc.

The DTProviderHandler 15 is responsible for being able to route the indication to a DTServiceInterface object. A single provider handler is responsible for only those messages associated with a particular service. There are provider handlers for storage, verification, print, etc. The provider handler represents the division between the API layer of the toolkit and the internal software. The provider handler is responsible for either routing the message to an existing service interface object, or creating a new service interface object of the appropriate type and then routing the message on.

The DTServiceInterface object 16 on the service provider side of the network is responsible for performing any actions that the application determines is necessary to perform the actual DICOM service. It is the responsibility of the application developer to create a subclass of the appropriate DTServiceInterface class if the default behavior of the toolkit is not appropriate to the service that the application intends to carry out. Part of the default responsibilities of the DTServiceInterface object is to send an acknowledgment back to the service user side of the network. This outgoing message is called a "Response".

As on the user side of the network, the response is encoded into a DICOM message on the provider side of the network. This involves two processes. First, the message is formulated into the DICOM Toolkit's own internal representation which is call an element list. Each individual attribute that together comprises a message is represented in this list. The elements in the list then each in turn, dump themselves into packets specified by the DICOM protocol. The elements themselves, each know how to format themselves correctly. These packets are transmitted across a network (ethernet, fddi, etc.) to a DICOM service provider.

The incoming packets are decoded 18 by the service user, and an element list that is identical to the one that was transmitted is created on the user side. The incoming message is called a "Confirmation." The decoding process determines message type. This information is used to route the message to the correct DTUserHandler 19. Store Confirmation messages are routed to the DTStoreUserHandler. Verify Confirmation messages are routed to the DTVerificationUserHandler, etc.

The DTUserHandler 19 is responsible for being able to route the confirmation to the DTServiceInterface object that initiated the request to begin with. A single user handler is responsible for only those messages associated with a particular service. I.e., there will be user handlers for storage, verification, print, etc. The user handler represents the division between the API layer of the toolkit and the internals.

The DTServiceInterface object 11 on the service user side of the network is now responsible for performing any actions that the application determines is necessary to cleanup the transaction. At this point in time, the confirmation has been received, so the transaction is considered complete. It is the responsibility of the DTServiceInterface object to look at the status that was returned. If the status was success, the DTServiceInterface object may be cleaned up. If the status was not success, it is the responsibility of the application developer to determine how to recover from a bad status. Any of these actions could cause the application developer to need to create a subclass of the appropriate DTServiceInterface class.

All of user/provider handlers act out of the object-oriented call-back mechanism provided. Instead of the application registering call-back functions with the toolkit, the toolkit requires the application developer to create a subclass of specific class and override a specific method in order to effect a change with the toolkit's default behavior.

The toolkit of the present invention provides messages and appropriate DICOM values for sending and receiving DICOM standard protocol information and messages. The toolkit provides context-sensitive values. The toolkit provides for contextual interpretation of DICOM service requests. The toolkit adjusts messages and message parameter values to accommodate messages and which may be context sensitive, dependent upon the nature of the application which uses the toolkit framework.

The API Toolkit provides an Initialization Interface (II) comprising a C++ class that enables initialization of the toolkit for use with DICOM applications. II passes parameters to toolkit subsystems, specify default directory path names, register custom objects, and gain access to toolkit objects that enhance application performance. The C++ methods used to accomplish these tasks are part of class DTInitConfig, the base initialization class.

II provides methods of which many are optional and generally can be invoked in any order. II methods contain defaults so that the initialization process executes without changes in application code. In the minimum ease, two methods—init() and done()-are provided to signal the beginning and end of an initialization process. Initialization functions are accomplished within a single pass or loop.

II provides public methods which enable communication with important subsystems like the Resource Manager, the Communication Manager, and the Common Component Dispatcher (CCD). CCD enables use of a number of global objects that the toolkit generates. A user can easily derive subclasses to completely customize a toolkit application environment.

An initial method, init(), signals the beginning of an initialization process. The user specifies trace and error logs at this time. The toolkit provides a plurality of optional methods which pass parameters, set up default directories, and register custom objects. The done() method, checks selections and builds an application environment.

The following sections describes use of the initialization methods. The C++ class, DTInitConfig, is the DICOM Toolkit Interface object. It contains all of the methods available for use to initialize and configure the Toolkit. To use one of these methods, simply invoke it within application code.

The following briefly describes the DTInitConfig methods. The two required methods, init() and done(), mark the beginning and end of an application initialization sequence. Besides beginning the sequence, init() also provides a place to specify a path name for the trace and error logs. done() ends the initialization sequence and builds an application environment based on parameters and path names specified explicitly or with default values. The done() method ends the initialization process. These methods use the following syntax.

init()

virtual CCError init (const char *trcLogName, longtsize, longtflag, const char *errLogName, long eSize, long eFlag)const; *trcLogName is a pointer to the character string that contains the path name for the trace log. Similarly, *errLogName is a pointer to the path name for the error log. esize and tsize are the maximum sizes in bytes of the trace log and error log, respectively. tflag indicates whether or not to wrap the trace log. eflag indicates whether or not to flush the error log.

done()

virtual CCError done() const;

Get application-related objects

These methods enable access to global Toolkit objects including the element builder, the error handler, and two automatic file name generators. The first file naming object referenced below, ImageFileAutoNamer, generates unique temporary names for image files. The second, TempFileAutoNamer, enables generation of unique names for any temporary file.

These methods use the following syntax.
DTElementBuilder *getElementBuilder() const;
DTErrorHandler *getErrorHandler() const;
CCFile *getImageFileAutoNamer() const;
CCFile * getTempFileAutoNamer() const;

These methods enable the Toolkit to use any customized service handlers created within an application. To use these methods, provide a handler pointer for any desired custom handler. These methods are optional.

Figure 3:
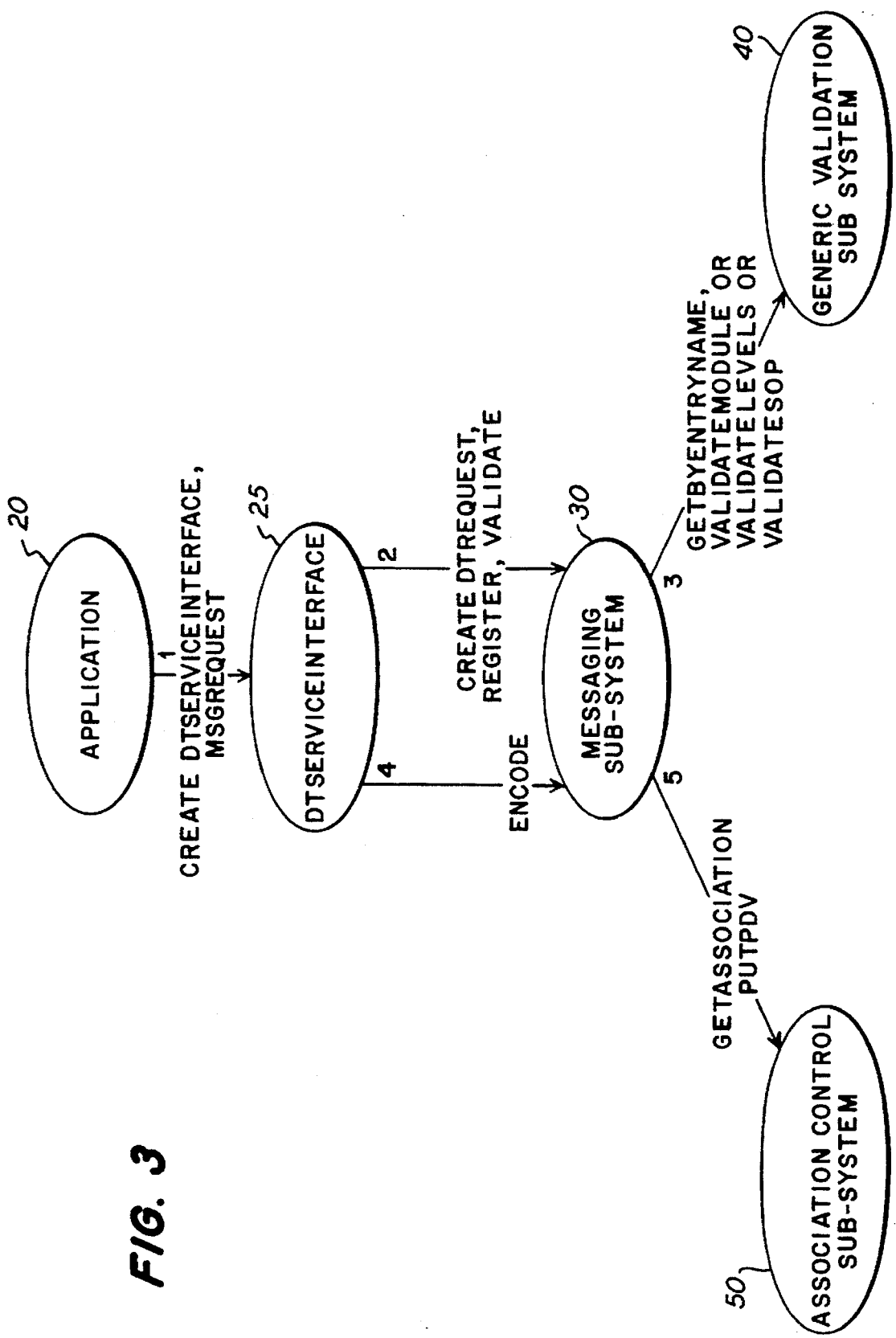
FIG. 3 a specific scenario illustrating an application implementing a DICOM service request.

These methods use the following syntax:

void SetPrintProviderHandler(DTPrintProviderHandler *handler)const;

void setPrintUserHandler(DTPrintUserHandler *handler) const void setQueryRetrieveProviderHandler (DTQueryRetrieveUserHandler *handler)const;\ void setQueryRetrieveUserHandler (DTQueryRetrieveUserHandler *handler)const;

void setStoreProviderHandler(DTStoreProviderHandler *handler)const;

void setVerificationProviderHandler (DTVerificationProviderHandler *handler)const;

void setNegotiatior(DTNegotiator *negtr) const;

Turning now to FIG. 3, an example of an application implementing a DICOM service is illustrated. In general, DICOM service scenarios comprise four (4) parts:

1) SCU generates Request by an application SCU;

2) the request is received as an "indication" by an SCU on the network;

3) SCP sends a response back over the network; and 4) the response is received by the requesting SCU, as a "confirmation."

FIG. 3 illustrates a simple scenario in which an application 20 selects create DTServiceInterface, and msgRequest to issue a request message. DTServiceInterface is the base class for images, queries and printer objects. The application is not involved in the remaining processing involved in creating and issuing the request message. The toolkit creates and issues the request message. DTServiceInterface 25 receives the create DTServiceInterface; and msgRequest from the application 10. DTServiceInterface 20 sends: a create DTRequest; a register; and validate message to Messaging Sub-System 30; Messaging Sub-System 30 sends a getByEntryName, validateModule or validateLevels or validateSop message to the Generic Validation Sub-system 40. DTServiceInterface 20 sends an encode message to the Messaging Sub-System 30. The Messaging Sub-System 30 sends a getAssociation message, and a putPdv message to the Association Control Sub-system 50. Numerous other example object scenarios for implementation of DICOM services are illustrated in the software microfiche appendix.

A message exchange subsystem is provided to implement the DICOM message exchange services, which provide the ability to create a command or corresponding status for each service the primitive command type. This subsystem supports the creation and deletion of commands and status as described in part 7 of the DICOM standard. The message exchange subsystem also provides for coordination of sending, receiving, encoding and decoding of commands and status describe in DICOM part 7.

The toolkit supports services as defined in the DICOM standard. These services or Service Objects comprise the DICOM services: VERIFY; STORE; QUERY/RETRIEVE; STUDY CONTENT NOTIFICATION; PRINT MANAGEMENT; PATIENT, VISIT, STUDY; and RESULTS MANAGEMENT. In general, the major DICOM services provided by the toolkit framework of the present invention comprise: general association, initialization and shutdown; buffer movement into and out of an open association; message element construction via stream parsing or application creation; message segment "editing" via message element addition or removal; command and response message construction; command and response send/receive; information object construction; validation; remote attribute setting/getting and remote actioning; composite information objects; normalized service-class objects; wide-area network support for transport of association control protocol; information model specification for use in validation queries; file services capable of storing/retrieving information objects; information object databases (application and network database, of which, a network database service comprises query/retrieve) and query-by-UID services.

The toolkit provides a set of objects with its framework which supports creation and maintenance of a DICOM database. This feature enables creation of application programs which manipulate DICOM information and support query/retrieve and query-by-UID services. The toolkit provides an object within its framework which supports a print session IO. A print session IO encapsulates a basic film session, corresponding basic film boxes and corresponding basic image boxes into a queryable IO. This feature enables programmers to create applications which manipulate DICOM information and support query/retrieve and query-by-UID services.

The toolkit provides an internal file subsystem. The file subsystem provides a generic application interface for manipulating DICOM files. The file subsystem, however, instead of using a DICOM defined directory, generates an abstract directory based on a common-denominator of the platforms which are using a DICOM directory. The abstract directory contains sub-directories or DICOM files. In mapping the DICOM standard file-set to the toolkit abstract directory, any directory may be designated as a file-set,file-set, if that directory contains a DICOMDIR file.

The toolkit provides a message exchange subsystem. The toolkit also provides an object which provides a presentation subsystem. The presentation subsystem provides extended functionality. For generic validation purposes, the message exchange subsystem, using a DICOM directory subsystem, interprets the DICOM standard, part 4 service specification's status category "refused" as "failed." The toolkit also provides an association subsystem which differs from the DICOM standard requirements. The association subsystem provides a means for assigning attributes to a static UID (e.g., transfer syntax, abstract syntax, etc.). One of the attributes is "vendor type." This attribute facilitates a mapping of a third party vendors' UIDs to the UIDs of the toolkit, the local PACS and the DICOM standard.

The toolkit provides an information object subsystem which supports implementation of DICOM standard part 4 services. The toolkit enables a programmer to create composite and normalized information objects and query/query-result data sets. The toolkit enables the use of information objects and the data sets which underlie them as toolkit entities. The information object subsystem enables an application to directly manipulate information objects. The toolkit provides an application program with direct access to DICOM services which apply to a particular information object. In a preferred embodiment, the toolkit provides a direct means by which an application can store an information object. The toolkit enables manipulation of pixel or overlay data. Pixel data may be compressed, packed, padded, or byte-swapped. Spare bits in a "bits allocated" space are used to store overlay planes.

The messaging subsystem provides DICOM services for STORE of SCUs and SCPs. The messaging subsystem provides composite information objects types: basic study descriptor; computed radiography; computed topography; magnetic resonance; nuclear medicine; print session; secondary capture; and ultra-sound. The messaging subsystem provides Print management services for SCUs and SCPs. The toolkit supports normalized information object types: basic film session; basic film box; basic image box; basic annotation; image overlay box; printer and print job.

The toolkit provides DICOM QUERY/RETRIEVE services for both SCUs and SCPs. The toolkit provides information model types: patient root; study root; print/study-only; print session-root; and print session. The present invention provides an information object database subsystem which enables applications to provide general database functions: navigation, insert, delete, insert/query and modify. This database is constructed using the DICOM attribute hierarchical model.

A toolkit database is provided which contains database-level objects. Each object contains attributes unique to its corresponding database level. Lower-level (children) objects are contained in a single parent higher-level object through the use of an implementation-specific collection mechanism. As new products or interfaces are created or older ones modified, a database application uses the toolkit database object definition to incorporate new and/or modified database entries. The application programmer identifies which DICOM or DICOM-like attributes reside in a database and the type of database hierarchy upon which the database is implemented. The toolkit enables an application programmer to express the semantics of the database hierarchy.

A database instance provides services for application users and network users. Application user database functions enable applications to navigate a database, change database objects, insert new database objects or delete current database objects. Network user database functions are restricted to a DICOM Standard defined QUERY/RETRIEVE Service. The toolkit enables a user to specify a database implementation based on a user-defined hierarchical information mode (HIM). The HIM is comprised of DICOM attributes. The toolkit implements each database instance with one type of HIM. A toolkit user specifies the semantics for the HIM. The toolkit provides an application/product specific database structure by which an application controls changing of database structures and indices. The DICOM directory provided by the toolkit provides user folders at any level in the database.

The present invention provides commonly used interface/process-level functional methods for providing DICOM services. These user handler enables an application to send a user-specified DICOM-encoded file message to a specified destination using the association control protocol. A provider handler receives the user-specified DICOM-encoded SEND message from an open association, stores the data set in a file, and reports to the requesting application ("call back"), upon completion of the requested service, storage of the file. DICOM commands FIND or MOVE allow simple data base queries concerning the images stored at a particular node. DICOM PRINT MANAGEMENT requests initiate creation and printing of a film session, create and provide a visual summary of printing activities.

The toolkit provides processing of pixel and overlay data. Processing comprises: byte order, pixel data packing/unpacking, pixel data padding/unpadding, internal/external overlay conversion, compression/expansion, non-square pixels, multi-planar/interleave pixel data conversion, and multi-frame pixel/overlay data separating/combining. The toolkit also provides a file subsystem which enables machine/operating system independent file services. This subsystem combines application programmer interfaces provided by Mac System 7, Sun Solaris 2.3+ and Motorola System V in a single, event-driven synchronous+ asynchronous application programmer interface. The application programmer interface provides an optional asynchronous interface for all DICOM services. This option provides a performance boost for selected Macintosh applications, for example, mount services (mount and unmount); directory services (creating, renaming, deleting and iterating through entities), directory and file services (creating, renaming and deleting) and open file services (opening, closing, reading data and writing data).

The toolkit provides non-genetic SOP-class specific application validation. The toolkit also provides a direct means to access commonly used information object attributes, and provides for the mapping of UIDs to data sets. The toolkit provides a method by which an application program maintains a relationship between active information objects and the UIDs that reference them.

The toolkit enables association management. In a preferred embodiment, messages destined for a particular application entity in supporting an SCU-SCP pair for an SOP, ate sent over an existing association, or over a new association created based upon the following conditions: A message is sent to an existing association as part of a META-SOP in progress which requires a message to be sent over a particular association; A message is sent over an existing association as a response to a previously sent request; A message is sent over a newly created association because no association to a specified destination exists; a message is sent over a new association as a C-Move request, which according to the DICOM standard, must be sent over a different association; or a message is not sent because an application entity is judged down or because there are insufficient resources to support the message transfer.

The association management subsystem accounts for the asynchronous nature of opening an association. The association management subsystem does not attempt to reopen a new association when another association is already opened to a particular destination. Destinations are considered "down" which frequently reject request or are closed, due to an unexpected close of a connection. A destination can be considered "up" due to a time lapse or by an application request. Associations that have not been frequently used can be shutdown due to the occurrence of a send- or receive-idle time-out. An idle time-out occurs when there are no outstanding transactions on an association and a specified period of time has expired since a message was sent to or received from the association.

The present invention provides a message management function comprised of several subcomponents. One subcomponent of message management provides a means to relate DICOM transactions to open associations. This subcomponent facilitates mapping of status to corresponding commands and mapping C-Sends to corresponding C-Moves. Message management insures that outstanding transactions are terminated upon shutdown of a association. Other message management subcomponents control the rate of delivery ("throttling") and the number of outstanding transactions sent or received over an open association. These subcomponents adjust message delivery rates based upon previously negotiated SCP-SCU roles after determining the SCP-SCU role for an incoming network message. Throttling may be interactively controlled as well using an interactive control loop, with feed back in the form of messages based on system load conditions. The message handling subsystem supports negotiation of SOP-specific negotiables (listed by DICOM service) and provides for negotiation of SCP-SCU roles and the asynchronous message delivery rate or throttle window at an association level.

The toolkit provides a presentation subsystem. The presentation subsystem comprises message segment encode/decode and generic validation. Generic validation comprises element syntax, for the DICOM standard parts 5 and 6, and generic validation of generic semantics as described in DICOM standard parts 3, 4, and 7. Message segment encode/decode includes support for specific element encoding/decoding for the following types: application entity, attribute tag, date, floating-point single, integer string, long text, other byte, person name, short string, signed short, time, and unsigned long. Message segment encoding/decoding also includes support for the following interface types: Create, Destroy, Encode (a DICOM stream or text stream), Decode (a DICOM stream or text stream), Insert (element), Remove (element), Compare (two element data values), and Match against (explicit or wild card) element (identifier) values.

EXAMPLES OF USE

The following is a generalized example using the toolkit.

The following steps perform sending an application-created image:

a. An application requests creation of image object;

b. the application requests creation of element subobjects;

c. the application requests adding values to elements subobjects;

d. the application requests insertion of element subobjects into image object; and e. the application requests the image object send itself to destination XYZ.

The following steps should be taken to report to an application that an image has been received:

a. Inform toolkit as to receive preferences, representation format (i.e. receive format), whether partially formed objects are to be reported or not;

b. the application gets called-back and handled fully or partially formed image object;

c. the application can then manipulate image. The application is responsible for keeping track of the fact the image may not be fully formed and must react appropriately should image sub-objects turn up 'missing'. Toolkit provides a means for an application to determine whether or not an object is complete.

The following steps should be taken for generating a query (or query response):

a. Application requests creation of a query (response) object;

b. Application requests creation of key/identifier element subobjects;

c. Application requests adding values to elements subobjects;

d. Application requests insertion of element subobjects into query (response) object; and e. Application requests query (response) object send itself to destination XYZ.

The following steps should be taken for handling a query:

a. Inform toolkit as to which application receives queries;

b. Application is called-back and handled (fully formed) query object; and c. Application gets key-identifier elements and begins matching them against a 'database'.

The following steps should be taken for basic printing:

a. Create a Film Session object (with N-CREATE);

b. Set attributes in that object, e.g., 'Number of Copies' (with N-SET). This tends to happen frequently when this object is reused for subsequent printing sessions within a given association; and c. Do one or more of the following (1, 2 or 3):

(1) Create a Film Box object related to the previous created Film Session (with N-CREATE). The act of creating a film box implies that a sequence of child Image Boxes was also created. Also note that it is the responsibility of the SCU at creation time to pass the applicable 'Annotation Display Format Id'. The act of setting this Id causes a sequence of child basic Annotation objects to also be created. Note that this step can be eliminated if Film Box objects are reused.

(2) If previously negotiated, creates a Perception look-up-table object related to the film box with "N-CREATE."

(3). If previously created, set attributes in one or more Basic Annotation objects related to the film session (with N-SETs).

(4). Set attributes within the film box object e.g. 'border density' (with N-SET).

(5). For some film box objects, do one or more of the following:

(i) Set attributes within a image box object. This includes elements associated with pixel presentation. This also includes the essential information within a preformatted-print image. This step can be eliminated if Image Box objects are reused.

(ii). If previously negotiated, perhaps created a VOI LUT object related to the image box (with the N-CREATE method).

(iii) If previously negotiated, perhaps created one or more Image Overlay objects (with N-CREATEs).

(6). Print a Film Box object (with N-ACTION). A corresponding Print Job object is created as a side-effect. d. Print the Film Session (with N-ACTION). A corresponding Print Job object is created as a side-effect.

(7). If previously negotiated, receive events or get attributes from Print Job or Printer objects.

The software microfiche appendix contains a breakdown of the objects and classes involved with implementing the toolkit, which includes a breakdown at a layer (library-like) level for each class (roughly a source file+include file) and the dependencies between classes.

It is recognized that a person of skill in the art can take this specification and make modifications to alter the order in which steps are performed or alter the steps of a process in order to change the resulting structure or method while staying within the scope of the claimed invention.

What is claimed is:

1. A method for creating application programs that provide DICOM services on a computer comprising the steps of:

(a) providing a framework of service objects mapped to a DICOM standard;

(b) providing a baseclass for each service object in the framework;

(c) deriving a plurality of related service objects from the framework;

(d) providing a service handler and service provider for each derived service object;

(e) providing an application interface to the framework of service objects;

(f) accepting from the application interface a request for service request to generate an application program to provide the requested service;

(g) determining a set of related objects to perform the requested service;

(h) providing a first mapping from the related service objects to a set of methods which perform a selected service;

(i) providing a DICOM service by invoking the execution of the related objects selected by the mapping; and (j) providing a unique association between the service handler and the service provider;

(k) providing a map between the association and the service handler and the service provider;

(l) providing object-oriented call-backs between the service handler and the service provider; and (m) sending and receiving messages between the service handler and the service provider over the unique association;

(n) instantiating a service object;

(o) providing a service class provider;

(p) providing a unique association between the service object and service class provider; and (q) providing a service interface object to encapsulate information and data.

2. The method of claim 1 further comprising the steps of:

(j) providing a transport layer;

(k) providing an association layer;

(l) providing a presentation layer;

(m) providing a service primitives layer; and (n) providing an information object layer.

3. The method of claim 1 wherein the step of providing an application layer further comprises the steps of:

reading a unique identifier from a service request;

providing a data base containing unique identifier context information;

negotiating a unique context having specific service class provider and service class user roles;

providing a data dictionary; and validating message elements against the data dictionary.

4. The method of claim 3 further comprising the steps of:

assigning attributes to unique identifiers comprising a mapping between a service request and applications available within the PACS.

5. The method of claim 1 wherein the step of providing an information object layer further comprises the steps of:

validating information object semantics and construction;

setting/getting attributes remotely; and validating syntax.

6. The method of claim 5 further comprising the steps of:

providing an information model type for each patient root, study root, print/study-only, print session-root, and print session; and providing an information object type for each basic study descriptor, compute radiography, computed topography, magnetic resonance, nuclear medicine, print session, secondary capture, and ultra-sound.

7. The method of claim 1 further comprising the steps of:

providing a data base implementation base on a user-defined hierarchical information model comprised of DICOM attributes; and enabling an application to change existing structures and indices.

\* \* \* \* \*